(12) United States Patent
Williams (10) Patent No.: US 9,022,213 B2
(45) Date of Patent: May 5, 2015

(54) MEDICAL DEVICE RETRIEVAL KIT

(71) Applicant: Jamie Williams, Manheim, PA (US)

(72) Inventor: Jamie Williams, Manheim, PA (US)

(73) Assignee: Robson Forensic, Inc., Lancaster, PA (US)

( * ) Notice: Subject to any disclaimer, the term of this patent is extended or adjusted under 35 U.S.C. 154(b) by 166 days.

(21) Appl. No.: 13/657,276

(22) Filed: Oct. 22, 2012

(65) Prior Publication Data

US 2013/0105337 A1 May 2, 2013

Related U.S. Application Data

(60) Provisional application No. 61/552,659, filed on Oct. 28, 2011.

(51) Int. Cl.
  *B65D 81/24* (2006.01)
  *B65D 81/26* (2006.01)
  *B65D 81/02* (2006.01)
  *A61F 17/00* (2006.01)

(52) U.S. Cl.
  CPC ..................... *A61F 17/00* (2013.01)

(58) Field of Classification Search
  CPC ......... A61F 17/00; A61F 2/0095; A61F 2/36; A61F 2250/0085; A61F 2002/3071
  USPC ............... 206/438, 570, 440, 210, 524.4, 205
  See application file for complete search history.

(56) References Cited

U.S. PATENT DOCUMENTS

| 3,255,871 | A | | 6/1966 | Butler |
| 4,011,947 | A | | 3/1977 | Sawyer |
| 5,087,450 | A | * | 2/1992 | Lister ............................ 424/402 |
| 5,236,088 | A | | 8/1993 | Dhority et al. |
| 5,868,245 | A | * | 2/1999 | Alt ................. 206/210 |
| 6,119,855 | A | * | 9/2000 | Yeager et al. .............. 206/213.1 |
| 7,380,658 | B2 | * | 6/2008 | Murray et al. ................. 206/364 |
| 2002/0104774 | A1 | * | 8/2002 | Hammond .................... 206/570 |
| 2004/0055925 | A1 | * | 3/2004 | Franks-Farah et al. ....... 206/570 |

* cited by examiner

*Primary Examiner* — Mickey Yu
*Assistant Examiner* — Chun Cheung
(74) *Attorney, Agent, or Firm* — McNees Wallace & Nurick LLC (57) ABSTRACT

A kit for the packaging and shipping of components of an explanted medical device. The kit includes sealable containers to individually package the components of the explanted medical device. The kit also includes dressing presoaked in a preservation fluid, the dressing being provided in at least one sealed container prior to the removal of the explanted medical device to maintain the dressing a presoaked, sterile condition. The amount of preservation fluid applied to the dressing is controlled, thereby eliminating the need for a reservoir of fluid to be provided.

16 Claims, 9 Drawing Sheets

FIGURE 1

LIST OF HIP RETRIEVAL PACKAGING KIT CONTENTS

This kit contains the following materials:

1) One (1) temperature controlled box
2) One (1) sheet protector
3) One (1) document entitled "ATTENTION PATIENT: Hip Retrieval Instruction Sheet"
4) One (1) form entitled "Hip Patient Information Sheet"
5) One (1) document entitled "ATTENTION SURGEON: Hip Retrieval Packaging Instruction Sheet"
6) One (1) Pre-Addressed Shipping label
7) One (1) 10% Buffered Formalin Material Safety Data Sheet
8) One (1) large sealable biohazard bag
9) Four (4) labeled sealable biohazard bags
10) Four (4) sterile gauze soaked in 10% Formalin solution
11) Four (4) pieces of bubble wrap
12) Four (4) cold packs

FIGURE 2

ATTENTION PATIENT:
Hip Retrieval Instruction Sheet

This kit contains all of the materials to package and ship your explanted hip implant to for nondestructive inspection, handling and storage.

Instructions for Hip patients:

1) Prior to your revision surgery, complete the enclosed Hip Patient Information Sheet.

2) Place a copy of the completed Hip Patient Information Sheet in the sheet protector provided to be packaged and shipped with your retrieved Implant.

3) Review and discuss the Hip Retrieval Packaging Instruction Sheet with your attorney and with your orthopaedic surgeon prior to your revision surgery.

4) Bring this kit and the Hip Retrieval Packaging Instruction Sheet to your revision surgery and request that the retrieved (explanted) Implant be packaged per this protocol.

5) Ask for your packaged Implant to be shipped using the enclosed Federal Express slip or label.

6) If you have any questions, please contact                at

FIGURE 3

Hip Patient Information Sheet

1. Today's date: _______________
2. Patient's Name: _______________
   a. Date of Birth: _______________
   b. Gender: ☐ Male  ☐ Female
   c. Address: _______________
   d. Phone number: _______________
   e. Email: _______________
3. Attorney Name: _______________
   a. Firm Name: _______________
   b. Address: _______________
   c. Phone number: _______________
   d. Email: _______________
4. Revision Hip Surgery:
   i. ☐ Left Hip  ☐ Right Hip
   ii. Date of Surgery: _______________
   iii. Surgeon's Name: _______________
   iv. Phone number: _______________
   v. Email: _______________
   vi. Hospital where surgery was performed: _______________

FIGURE 4

ATTENTION SURGEON:
Hip Retrieval Packaging Instruction Sheet

Retrieval Packaging contents:
1. One (1) temperature controlled box (Note: This is the box which contains all supplies. Do not dispose of the box.)
2. Four (4) sterile gauze soaked in 10% Formalin solution
3. Four (4) labeled sealable biohazard bags
4. Four (4) pieces of bubble wrap
5. One (1) large sealable biohazard bag
6. One (1) Hip Patient Information Sheet
7. One (1) sheet protector for Hip Patient Information Sheet
8. Four (4) freezer packs
9. Shipping label (pre-addressed)
10. Formalin material safety sheet and safe handling instructions

* IMPORTANT:** Shipper must keep the included freezer packs frozen until the retrieved explant is ready to be shipped.

* IMPORTANT:** Please DO NOT ship explant on a Friday. In event of a Friday surgery, please keep freezer packs and explant frozen for shipping on the following Monday.

*** Do not sterilize the components. Immediately (in Operating room) wrap explanted components and package as follows:

Instructions for packaging explants:
1. Read the enclosed Formalin material safety sheet and safe handling instructions.
2. Wrap all components individually in formalin soaked sterile gauze. (Provided)
3. Place each component in individual labeled sealable biohazard bags and seal shut. (Provided)
4. Bubble wrap each individual bag and place in large biohazard bag (Provided) and seal shut.
5. Place two (2) cold pack in the bottom of the temperature controlled box.
6. Place the large biohazard bag, with contents, into the temperature controlled box.
7. Place two (2) cold pack on the top of the large biohazard bag.
8. Place the plastic sheet protector enclosing the completed Hip Patient Information Sheet into the box.
9. Using the pre-addressed label provided, ship via FedEx.
10. Please call ______ to notify ______ when package is shipped.

If you are unable to follow these Instructions please keep the explants refrigerated and call ______ immediately.

FIGURE 5

LIST OF RETRIEVAL PACKAGING KIT CONTENTS

This kit contains the following materials:

1) One (1) temperature controlled box
2) One (1) sheet protector
3) One (1) document entitled "ATTENTION PATIENT: Retrieval Instruction Sheet"
4) One (1) form entitled "Patient Information Sheet"
5) One (1) document entitled "ATTENTION SURGEON: Retrieval Packaging Instruction Sheet"
6) One (1) Pre-Addressed Skipping Label
7) One (1) 10% Buffered Formalin Material Safety Data Sheet
8) One (1) large sealable biohazard bag
9) Six (6) labeled sealable biohazard bags
10) Six (6) sterile gauze soaked in 10% Formalin solution
11) Six (6) pieces of bubble wrap
12) Four (4) cold packs

FIGURE 6

ATTENTION PATIENT:
Retrieval Instruction Sheet

This kit contains all of the materials to package and ship your explanted knee implant to for nondestructive inspection, handling and storage.

Instructions for knee revision patients:

1) Prior to your revision surgery, complete the enclosed *Patient Information Sheet*.

2) Place a copy of the completed *Patient Information Sheet* in the sheet protector provided to be packaged and shipped with your retrieved Implant.

3) Review and discuss the *Retrieval Packaging Instruction Sheet* with your attorney and with your orthopedic surgeon prior to your revision surgery.

4) Bring this kit and the *Retrieval Packaging Instruction Sheet* to your revision surgery and request that the retrieved (explanted) Implant be packaged per this protocol.

5) Ask for your packaged Implant to be shipped using the enclosed Federal Express slip or label.

6) If you have any questions, please contact

FIGURE 7

Patient Information Sheet

1. Today's date: _______________
2. Patient's Name: _______________
   a. Date of Birth: _______________
   b. Gender: ☐ Male   ☐ Female
   c. Address: _______________
   d. Phone number: _______________
   e. Email: _______________
3. Attorney Name: _______________
   a. Firm Name: _______________
   b. Address: _______________
   c. Phone number: _______________
   d. Email: _______________
4. Revision Knee Surgery:
   i. ☐ Left Knee   ☐ Right Knee
   ii. Date of Surgery: _______________
   iii. Surgeon's Name: _______________
   iv. Phone number: _______________
   v. Email: _______________
   vi. Hospital where surgery was performed: _______________

FIGURE 8

ATTENTION SURGEON:
Retrieval Packaging Instruction Sheet

Retrieval Packaging contents:
1. One (1) temperature controlled box (Note: This is the box which contains all supplies. Do not dispose of the box.)
2. Six (6) sterile gauze soaked in 10% Formalin solution
3. Six (6) labeled sealable biohazard bags
4. Six (6) pieces of bubble wrap
5. One (1) large sealable biohazard bag
6. One (1) Patient Information Sheet
7. One (1) sheet protector for Patient Information Sheet
8. Four (4) freezer packs
9. Shipping Label (pre-addressed)
10. Formalin material safety sheet and safe handling instructions \*\*\* IMPORTANT: Shipper must keep the included freezer packs frozen until the retrieved explant is ready to be shipped.
\*\*\* IMPORTANT: Please DO NOT ship explant on a Friday. In event of a Friday surgery, please keep freezer packs and explant frozen for shipping on the following Monday.
\*\*\* Do not sterilize the components. Immediately (in Operating room) wrap explanted components and package as follows:

Instructions for packaging explants:
1. Read the enclosed Formalin material safety sheet and safe handling instructions.
2. Please wrap all components separately using the provided formalin soaked sterile gauze. Soaked gauze has been provided for the metal femoral component, metal tibial component, polyethylene liner, patellar button, femoral stem (if separated from the femoral component) and tibial stem (if separated from the tibial component). If the stems are connected to the components, please ensure that all surfaces are wrapped with formalin soaked sterile gauze. In the case that components are fractured, please wrap each fractured piece individually.
3. Place each component in individual labeled sealable biohazard bags and seal shut. (Provided)
4. Bubble wrap each individual bag and place in large biohazard bag (Provided) and seal shut.
5. Place two (2) cold pack in the bottom of the temperature controlled box.
6. Place the large biohazard bag, with contents, into the temperature controlled box.
7. Place two (2) cold pack on the top of the large biohazard bag.
8. Place the plastic sheet protector enclosing the <u>completed Patient Information Sheet</u> into the box.
9. Using the pre-addressed label provided, ship via FedEx.
10. 10. Please call _______ to notify _______ when package is shipped.

If you are unable to follow these instructions please keep the explants refrigerated and call _______ immediately.

FIGURE 9

MEDICAL DEVICE RETRIEVAL KIT

FIELD OF THE INVENTION

This invention relates to a kit which is suited for the handling and shipping of explanted orthopedic implants and/or other medical devices.

BACKGROUND OF THE INVENTION

When medical devices, such as orthopedic implants, are removed from patients ("explanted devices"), they must frequently be shipped to a third party for examination and/or analysis for a variety of reasons, including regulatory responses and determination of liability in civil court actions. These materials are potentially biohazardous to those individuals handling the items during retrieval, shipping and examination.

In the past, medical personnel responsible for returning explanted orthopedic devices had to package, label, and ship the items by using packaging and labels chosen at their own discretion, which were often less than adequate. Many packages were packed and labeled in a manner lacking protection for those handling the package from potentially contaminated material.

Several patents describe methods and devices for preserving and transporting biological materials or prosthetic devices. U.S. Pat. No. 3,255,871 to Butler is directed to the use of a translucent plastic bag in which a formaldehyde solution is formed in situ for preserving and transporting biological material. U.S. Pat. No. 4,011,947 to Sawyer describes a packaged prosthetic device and a packaging technique designed so that a prosthetic device will arrive at its ultimate position for installation in a sterile and clean condition.

U.S. Pat. No. 5,236,088 to Dhority et al. is directed to an orthopedic implant retrieval kit which, when assembled, provides a shipping and handling container for explanted orthopedic devices. The kit includes a container for holding a suitable level of formalin solution. The container is sealed within several other containers to prevent leakage. The multiple containers have absorbent material positioned thereabout to also prevent leakage.

There is a need to provide a retrieval kit in which tissue can be shipped in a secure, safe and non-degenerative manner across long distances and international boundaries. There is also a need to provide a retrieval kit in which the issue of leakage is essentially eliminated, thereby allowing the retrieval kit to be easily assembled and easily and securely shipped.

SUMMARY OF THE INVENTION

An embodiment is directed a kit for the packaging and shipping of components of an explanted medical device. The kit includes sealable containers to individually package the components of the explanted medical device. The kit also includes dressing presoaked in a preservation fluid, the dressing being provided in at least one sealed container prior to the removal of the explanted medical device to maintain the dressing a presoaked, sterile condition. The amount of preservation fluid applied to the dressing is controlled, thereby eliminating the need for a reservoir of fluid to be provided.

An embodiment is directed to a kit for the packaging and shipping of components of an explanted medical device. The kit includes sealable containers to individually package the components of the explanted medical device. The kit also includes dressing presoaked in a preservation fluid, the dressing being non-abrasive to the components of the explanted medical device, the dressing being inert with respect to the preservation fluid applied thereto, the dressing being provided in at least one sealed container prior to the removal of the components of the explanted medical device to maintain the dressing a presoaked, sterile condition. The amount of preservation fluid applied to the dressing is controlled, thereby eliminating the need for a reservoir of fluid to be provided.

An embodiment is directed to a kit for the packaging and shipping of components of an explanted medical device. The kit includes sealable containers to individually package the components of the explanted medical device. At least some of the sealable containers include labeled component containers which identify each component of the explanted medical device. The kit also includes dressing presoaked in a preservation fluid, the dressing being provided in at least one sealed container prior to the removal of the explanted medical device to maintain the dressing a presoaked, sterile condition. Packaging material and cooling devices are also provided. The packaging material protects the components of the explanted medical device during shipping. The cooling devices maintain the proper temperature of the components of the explanted medical devices during shipping. The amount of preservation fluid applied to the dressing is controlled, thereby eliminating the need for a reservoir of fluid to be provided.

An embodiment is directed to a kit for the packaging and shipping of an explanted medical device, the kit having individual packaging for all components of the explanted medical device.

An embodiment is directed to a kit for the packaging and shipping of an explanted medical device, the kit having presoaked dressing which is provided to be wrapped around individual components of the medical device.

An embodiment is directed to a kit for the packaging and shipping of an explanted medical device, the kit having an insulated box; sealable containers for receipt of components of the explanted medical device; presoaked dressing for wrapping the component; and a cooling device.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

FIG. 5 is an exemplary packing instruction sheet, the exemplary packing instruction sheet relates to a hip retrieval kit;

FIG. 9 is an alternate exemplary packing instruction sheet, the exemplary packing instruction sheet relates to a knee retrieval kit;

DETAILED DESCRIPTION OF THE INVENTION

Figure 1:
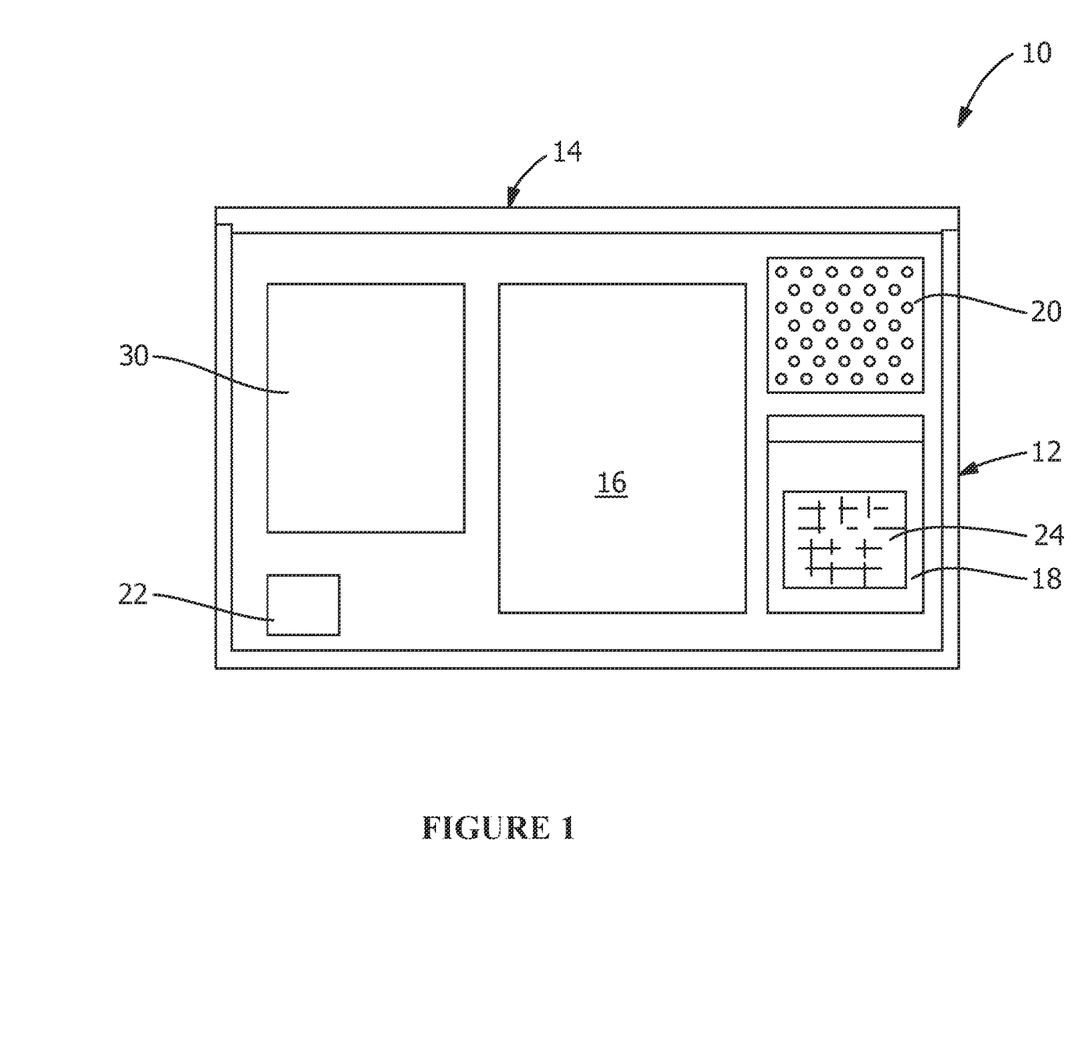
FIG. 1 is a diagrammatic sectional view of a box containing the assembled components of an orthopedic implant retrieval kit.

FIG. 1 shows components of medical device implant retrieval kit used for packing an explanted medical device, such as, but not limited to, implanted medical devices used for hip replacement, knee replacement, shoulder replacement, transvaginal mesh, hernia mesh, disk replacement, stents, catheters, ankle replacement, wrist replacement and spinal plates, rods, screws and cages. The components of the kit of FIG. 1 are shown prior to being utilized in the packing medical device and/or related tissue sample into a shipping container 10. The components of the kit are described below in conjunction with an exemplary method for packing such materials.

As shown in the exemplary embodiment of FIG. 1, the kit 10 includes an insulated or temperature controlled box 12 having a lid 14. Housed within the box 12 are one large sealable biohazard or specimen container or bag 16, six labeled sealable biohazard or component containers or bags 18 which are labeled to identify each component of the relevant explanted devices which is to be inserted therein, six pieces of packaging material or bubble wrap 20 and four cold packs 22. The kit depicted in FIG. 1 is for the retrieval of an explanted hip. Depending upon the medical device to be retrieved the number of the various bags, bubble wrap and cold packs may vary.

The bags 16 and 18 are of the type in which a sealing strip is provided at the top of the bag to seal the contents of the bag. One such bag is sold under the Ziploc trademark. However, other types of bags or sealing containers which provide an adequate seal can be used.

Although bubble wrap 20 is shown in the exemplary embodiment, other types of packaging material which adequately protect the explanted medical device and its components from damage during shipping can be used. In addition, the invention is not limited to the use of cold packs 22, as other types of cooling devices can be used.

Provided in the resealable component bags 18 is a dressing (s) or sterile gauze 24 which have been presoaked in a preservation fluid of approximately 10% buffered formalin solution. While the exemplary embodiment describes a preservation fluid of approximately 10% buffered formalin solution, other appropriate percentages or solutions may be used without departing from the scope of the invention. While in the embodiment shown the dressing is gauze, the term dressing is meant to include, but not be limited to, any type of fabric or other material which can be made sterile and which has the appropriate absorption and pliability characteristics required for use in the kit 10. In addition, the dressing must be inert with respect to the solution and tissue, and the dressing must be non-abrasive to the tissue which is packaged therein. The dressing may be provided in precut strips or pads or may be provided in a roll or the like which can be cut to size.

By providing presoaked dressing 24, the volume of preservation fluid or liquid which must be shipped in the kit is controlled and greatly reduced over kits shown in the prior art. This insures that the kits will not leak during handling and shipping, thereby facilitating the shipping of the kits 10 and allowing the kits 10 to be shipped by overnight courier or by other expedited means. In addition, due to the controlled nature of the formalin (i.e. the solution is not considered a hazardous material), the kits 10 are easily and routinely allowed to pass across international borders. As the explanted devices must be maintained at defined temperatures to prevent the degradation of the explanted devices, the kit must not be delayed during shipping. Consequently, the use of the presoaked dressing provides a safer, more effective means to preserve and ship the explanted devices.

Figure 2:
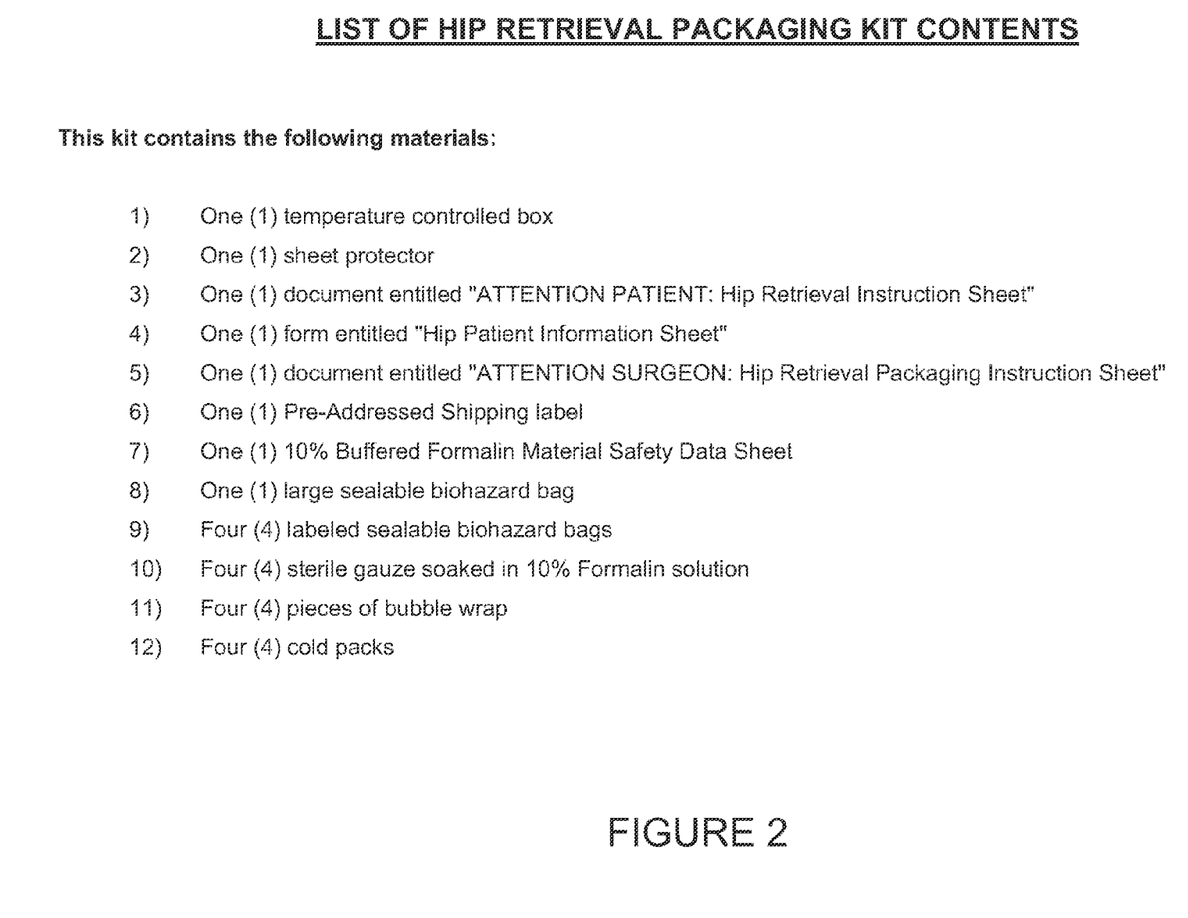
FIG. 2 is an exemplary list of the contents of an exemplary retrieval kit, the exemplary list relates to a hip retrieval kit.
Figure 3:
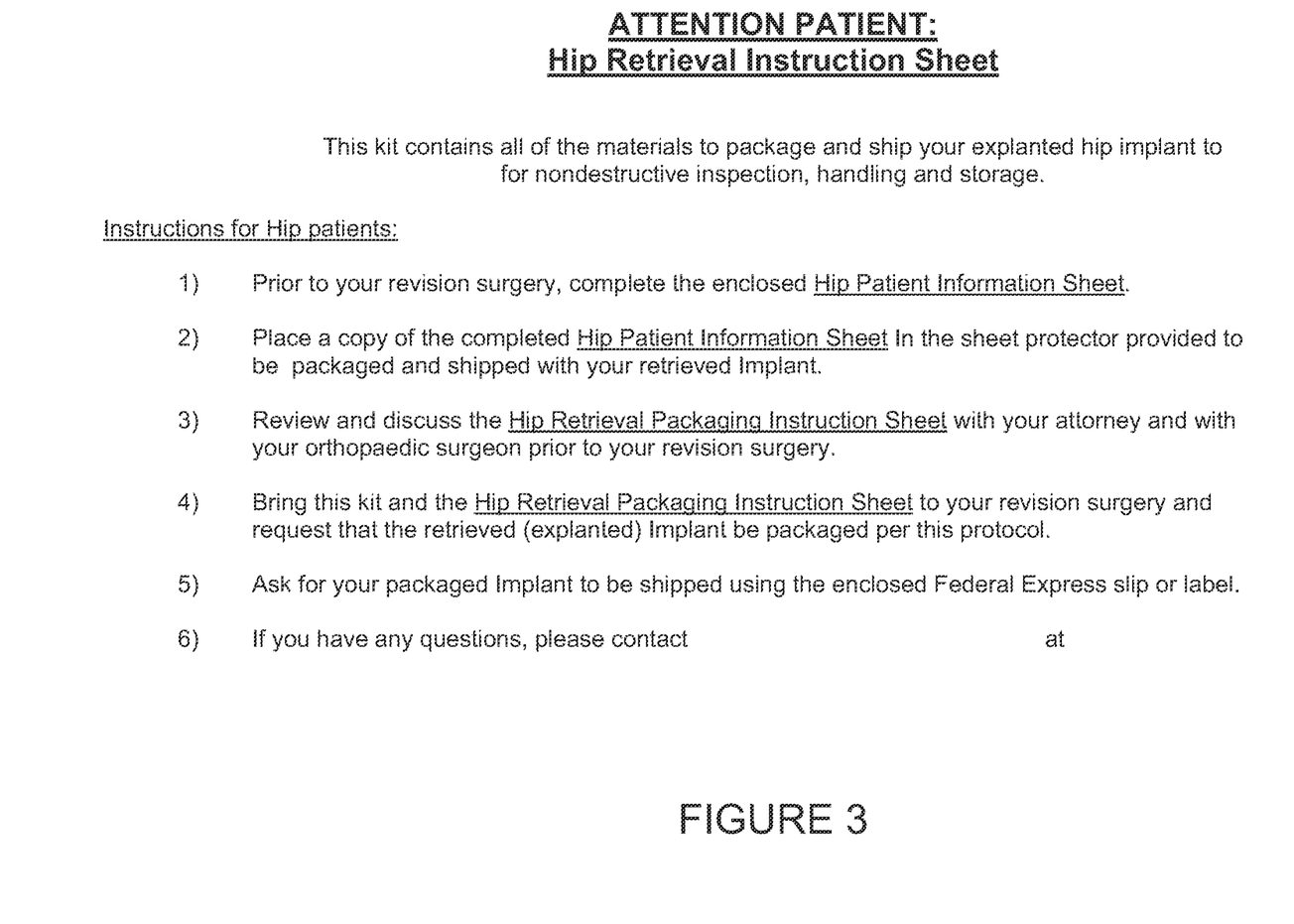
FIG. 3 is an exemplary patient instruction sheet, the exemplary patient instruction sheet relates to a hip retrieval kit.
Figure 4:
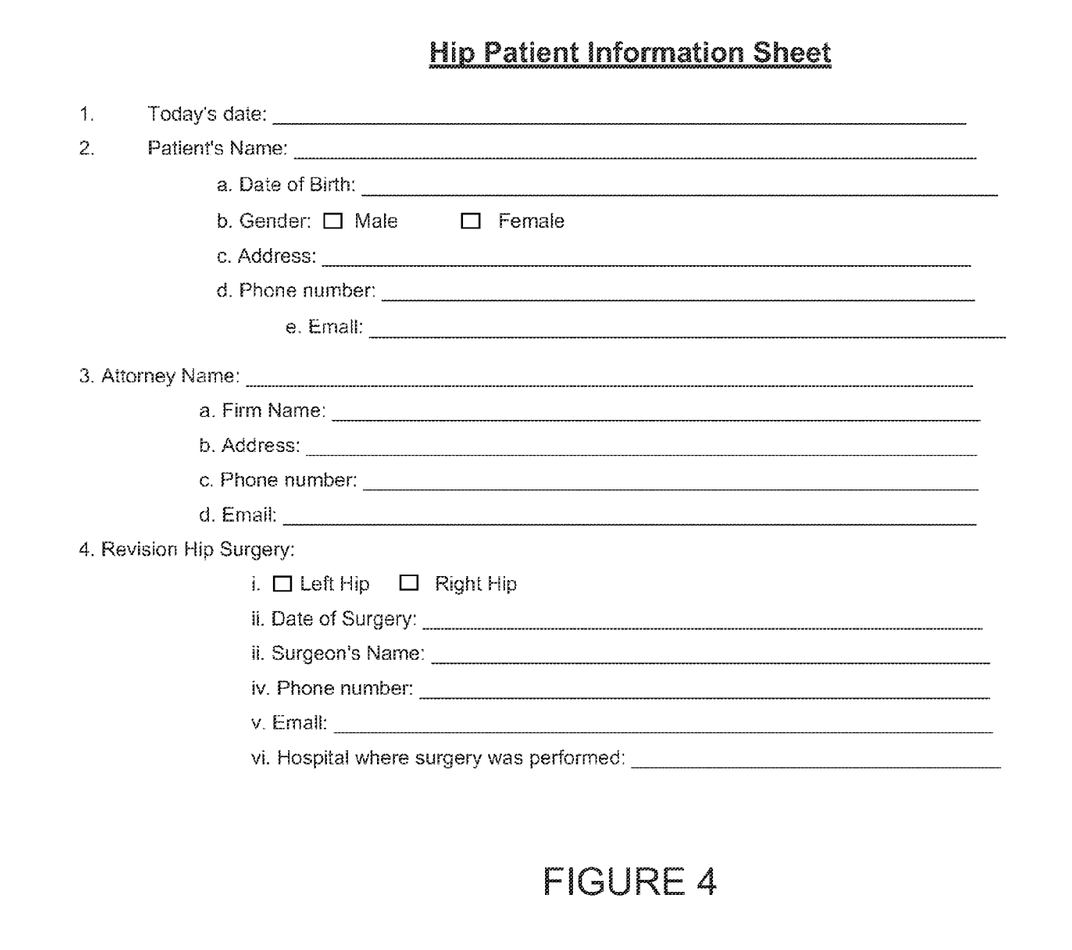
FIG. 4 is an exemplary patient information sheet, the exemplary patient information sheet relates to a hip retrieval kit.
Figure 6:
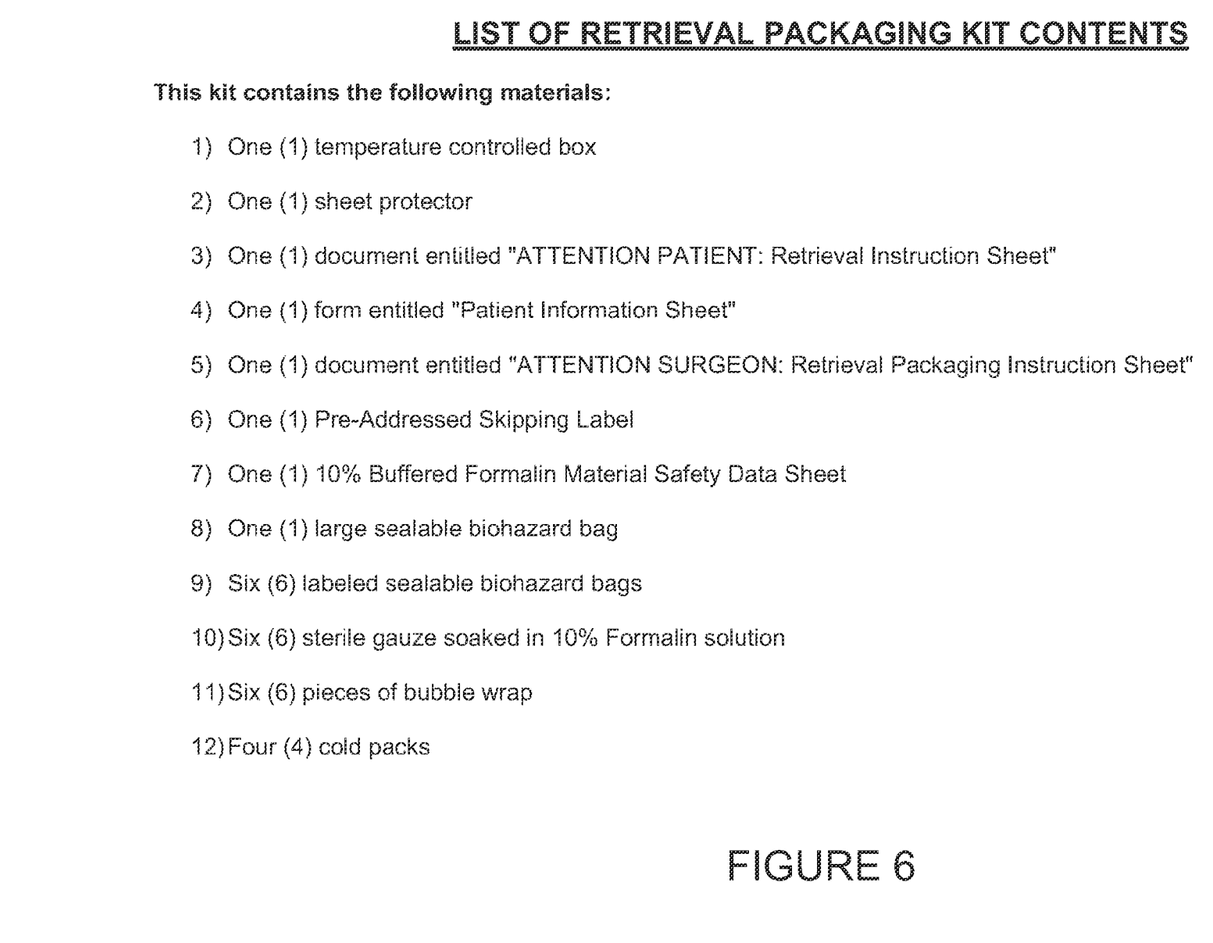
FIG. 6 is an alternate exemplary list of the contents of an exemplary retrieval kit, the exemplary list relates to a knee retrieval kit.
Figure 7:
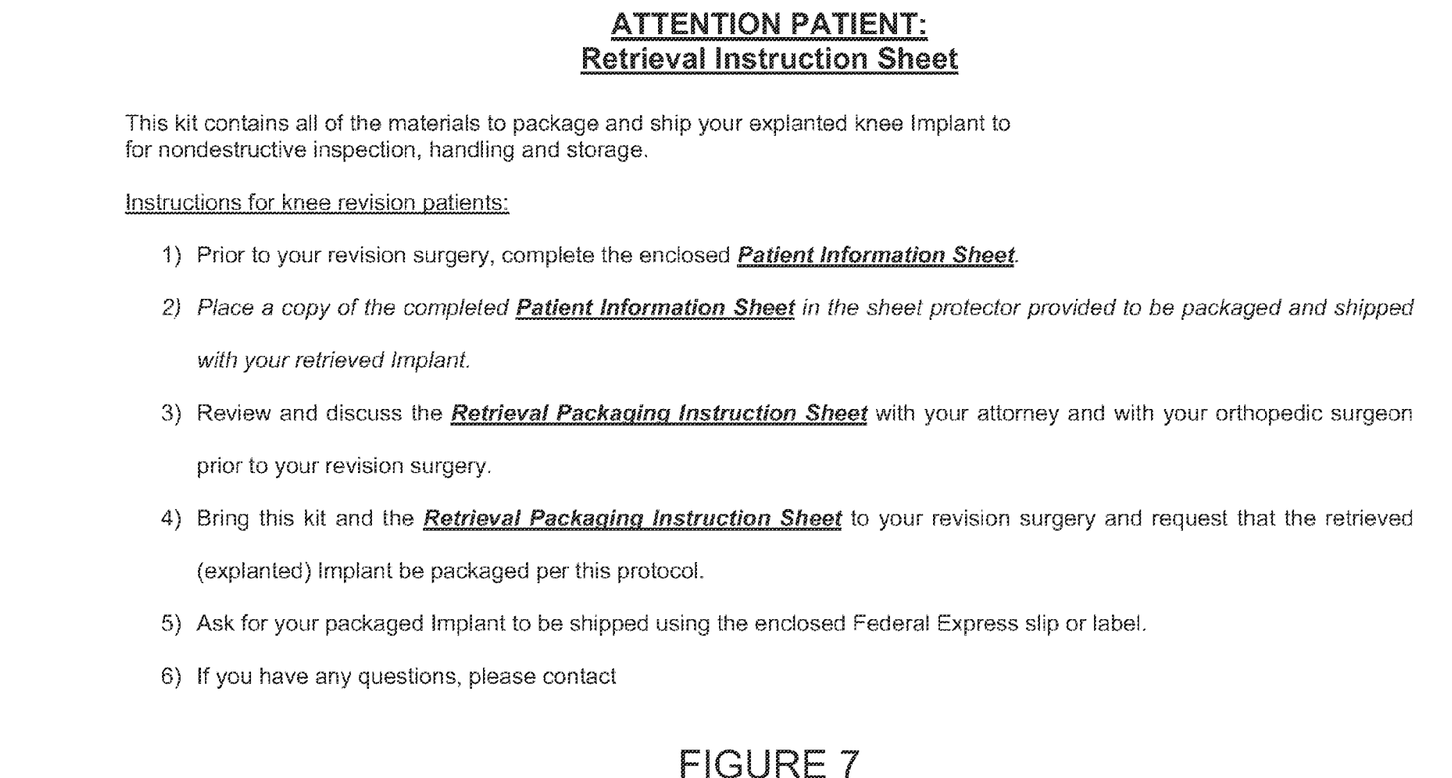
FIG. 7 is an alternate exemplary patient instruction sheet, the exemplary patient instruction sheet relates to a knee retrieval kit.
Figure 8:
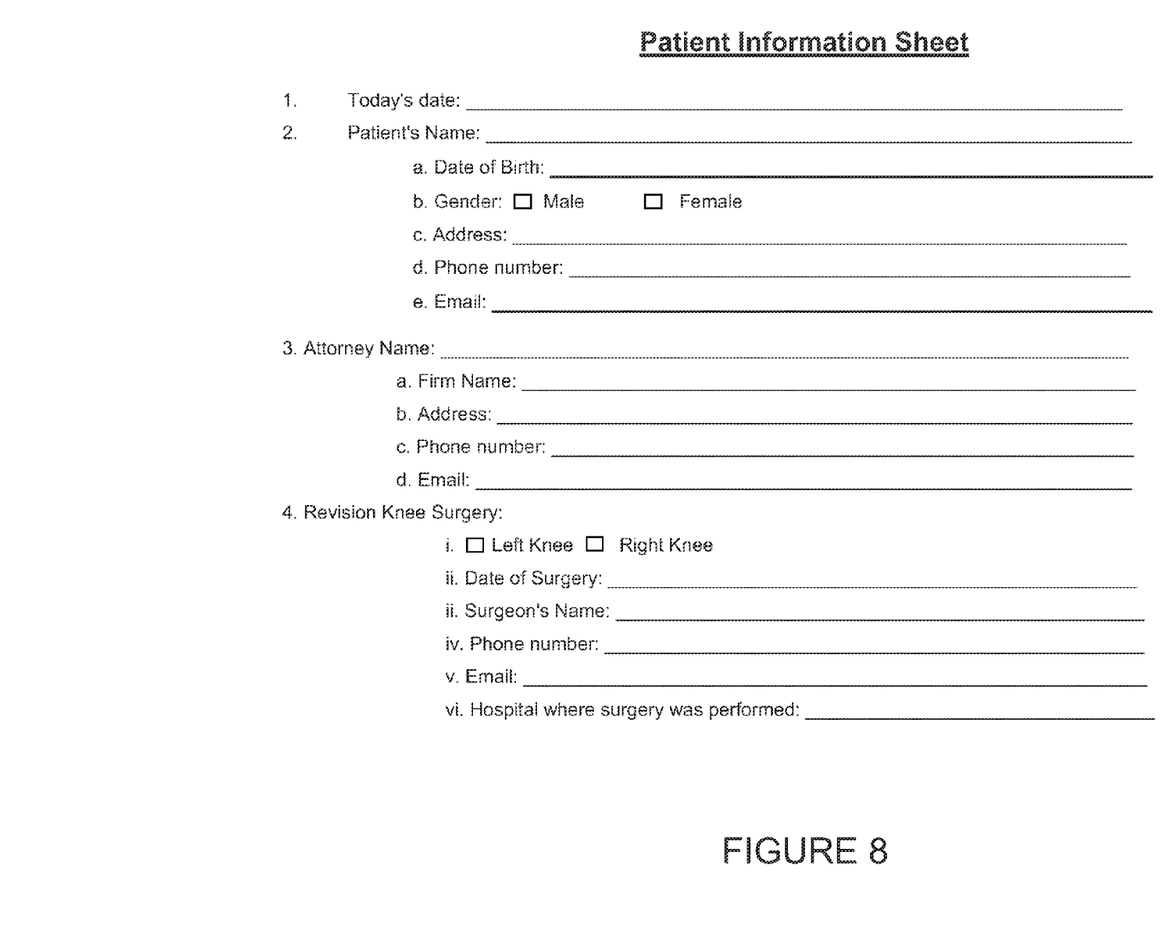
FIG. 8 is an alternate exemplary patient information sheet, the exemplary patient information sheet relates to a knee retrieval kit.

Also included with the kit 10 are materials or a packet of information which may be inserted into a sheet protector 30 or the like for protection against tears, moisture, or other types of damage. The materials or packet of information provides guidance regarding proper use of the kit and may include, but is not limited to: a list of the contents 32, as shown in FIG. 2; a patient instruction sheet 34, as shown in FIG. 3; a patient information sheet 36, as shown in FIG. 4; a packing instruction sheet 38, as shown in FIG. 5; a material safety data sheet (not shown) for any preservation fluid or chemical used, i.e. the 10% buffered formalin; and a pre-addressed shipping label (not shown). The kit 10 shown and described is merely a representative embodiment of such kits and other sheets and other wording can be used depending upon the type of device explanted.

In use, the kit 10 is generally sent to the patient or a representative of the patient. When sent, the bags 18, bubble wrap 20 and cold packs 22 are all provided in the box 12 with the lid 14 positioned thereon. The lid 14 and box 12 are sealed in any known manner to prevent the unwanted removal of the components. The pre-soaked dressing 24 is provided in one or more sealed bags 18 and remains therein until the dressing is applied to a component of a removed explanted device. This prevents the dressing 24 from being contaminated during shipping. In addition, as the bag or bags 18 are sealed, the preservation fluid solution will not evaporate from the dressing 24 during shipping, thereby allowing the dressing to remain soaked or moist during shipping. In so doing, additional solution is not required to be provided, as the presoaked dressing 24 remains moist. This eliminates the need to ship a reservoir of preservation fluid solution or liquid as required by the prior art.

Upon receipt of the kit 10, the patient follows the procedures recited on the patient instruction sheet 34 (FIG. 3). Once the patient information sheet 36 (FIG. 4) is completed, the patient provides the kit 10 to doctor or designee at the time of the revision surgery.

Upon completion of the surgery, in which the device has been explanted, the doctor or an appropriate member of the surgical or hospital staff follows the instructions for packaging and shipping of the explanted device.

Prior to handling the preservation fluid solution soaked dressing, it is recommended that the material safely and handling sheet (not shown) be read and understood so that proper safety handling procedures be followed.

All explanted components should be wrapped separately using the formalin soaked sterile dressing 24. In the exemplary embodiment shown in FIGS. 6 through 9, soaked gauze 24 is provided for the metal femoral component, the metal tibial component, the polyethylene liner, the patellar button, the femoral stem, and the tibial stem. It is important to note, that sufficient gauze 24 is provided to allow for fractured pieces to be individually wrapped. While the exemplary embodiment shown in FIGS. 6 through 9 describes procedures for explanted knees, instructions for all explanted devices require that all components be wrapped independently. This allows the proper examination of all components in an appropriate laboratory after the kit 10 has been shipped by the hospital.

With each component individual wrapped with the soaked dressing 24, each component is packaged or placed in the appropriate labeled component containers 18 and sealed shut. There is no need to place the components in a reservoir of liquid, as the presoaked dressing will properly preserve the bones and tissue. Packaging material 20 is then wrapped around each component containers 18. This insures that the individual components are protected from physical damage during shipping. Consequently, the use of the soaked dressing 24 and the packaging material 20 protect the components, insuring that the components will not be damaged or degraded during shipping. The wrapped components are then placed in the large specimen containers 16 and the specimen bag is sealed.

In the exemplary embodiment, two cold packs 22 are placed in the bottom of the temperature controlled box 12 to maintain the proper temperature of the components of the explanted device during shipping. The large specimen bag 16, with all the component bags 18 properly inserted, is positioned in the box 12. The additional two cold packs 22 are placed on top of the specimen bag 16. As previously discussed, the box may be cooled by different numbers of cold packs or by different cooling means.

The completed patient information sheet 36 is placed in the sheet protector 30 and placed on top of the cold packs 22. The lid 14 is then secured to the box 12. The preaddressed shipping label is mounted on the kit 10 and the kit 10 is shipped via courier or overnight service.

It should be noted that the sequence of packing the box 12 is merely one exemplary sequence. Other sequences can be used to pack the box 12 without departing from the scope of the invention.

The properly packaged and shipped explanted devices can be stored and/or examined at other facilities as needed or requested.

The kit provides a safe, effective and convenient method for shipping explanted medical devices. The sender, i.e. doctor, nurse, staff, only needs to package the material and send it. All of the materials needed are provided. The need to search for any of the necessary packing materials and the possibility of the packer using non-approved packing materials, are thereby eliminated. The instructions make clear the procedure to be followed. This allows all of the components of the explanted device to be properly preserved for later examination.

The use of kit 10 eliminates various problems associated with prior art kits. As an example, previous kits known in the industry required that all components be submersed in a formalin solution. This required a relatively large volume of formalin which led to increased leakage, thereby, causing difficulty in shipping, in particular shipping through customs. This problem is eliminated with kit 10, as the amount of preservation fluid applied or provided on the dressing is controlled, thereby eliminating the need for a reservoir of formalin.

The kit can be used with explanted medical devices, components, materials, tissue, instruments and/or other items such as, for example, but not limited to: i) total joint replacements for hip, knee, ankle, shoulder, intervertebral disc, elbow, wrist, finger, toe; ii) other orthopedic devices including plates, rods, screws, nails, hooks, wires, interbody fusion devices, cages; iii) other prosthetics including those made of silicone, metal, plastics or ceramics; iv) prosthetic devices including, but not limited to, eyeball prosthetics, teeth, other dental prosthetics, testicular, penal, breast implants; v) materials/scaffolds for the purposes of reconstruction and void fillers; vi) medical instruments including saws, hammers, screwdrivers, forceps, scalpels, clamps, drills, pain pumps and other internal monitoring devices; vii) cardiovascular implants, including, but not limited to, catheters, tubes, needles, sutures, staples, surgical adhesives; viii) cardiovascular including valves, shunts, stents, pace makers; ix) interuterine devices, implantable contraceptive devices, time release drug delivery systems, surgical meshes including but not limited to hernia meshes and transvaginal meshes; x) biological tissue including organ tissue, connective tissue, ligaments, tendons, muscle, bone, vascular tissues, nervous tissues, skin, hair and nails; and/or xi) biopsy materials including tumors, growths, moles, excised epidermal lesions and foreign bodies removed from the body.

While the invention has been described with reference to several preferred exemplary embodiments, it will be understood by those skilled in the art that various changes may be made and equivalents may be substituted for elements thereof without departing from the scope of the invention. As an example, as the type of explanted medical device changes, the amount of components may change, causing the number of containers to changes. In addition, the soaked dressing may be soaked in different chemicals depending upon the medical device and the advancement of the art. In addition, many other modifications may be made to adapt a particular situation or material to the teachings of the invention without departing from the essential scope thereof. Therefore, it is intended that the invention not be limited to the particular embodiment disclosed, but that the invention will include all embodiments falling within the scope of the appended claims.

What is claimed is:

1. A kit for the packaging and shipping of components of an explanted medical device which allows all of the components of the explanted medical device and associated materials to be properly preserved for later examination, the kit comprising:
   an insulated box;
   sealable containers to individually package the components of the explanted medical device;
   sterilized gauze dressing presoaked in a preservation fluid, the dressing is non-abrasive to the components of the explanted medical device and is inert with respect to the preservation fluid applied thereto, the dressing provided in at least one sealed container prior to the removal of the explanted medical device to maintain the dressing in a presoaked, sterile condition and to prevent the preservation fluid from evaporating from the dressing, the dressing being wrapped around each individual component of the explanted medical device subsequent to the removal of the explanted medical device to preserve the explanted medical device;
   cooling devices to maintain the components of the explanted medical devices at a temperature to prevent the degradation of the explanted medical device during shipping;
   whereby the amount of preservation fluid applied to the dressing is controlled, thereby eliminating the need for a reservoir of fluid to be provided.

2. The kit as recited in claim 1, wherein the preservation fluid is a formalin solution.

3. The kit as recited in claim 1, wherein the preservation fluid is a solution of approximately 10% buffered formalin.

4. The kit as recited in claim 1, wherein the sealable containers are bags with a sealing strip provided thereon.

5. The kit as recited in claim 4, wherein at least some of the sealable containers include labeled component containers which identify each component of the explanted medical device.

6. The kit as recited in claim 4, wherein the sealable containers include at least one sealable bag in which labeled component containers are inserted, thereby providing additional sealing.

7. The kit as recited in claim 1, wherein packaging material is provided in the kit, the packaging material protects the components of the explanted medical device during shipping.

8. The kit as recited in claim 1, wherein the kit includes materials which provide guidance as to the proper use of the kit.

9. A kit for the packaging and shipping of components of an explanted medical device which allows all of the components of the explanted medical device to be properly preserved for later examination, the kit comprising:

an insulated box;

sealable containers to individually package the components of the explanted medical device;

a sterile dressing presoaked in a preservation fluid, the dressing being non-abrasive to the components of the explanted medical device, the dressing being inert with respect to the preservation fluid applied thereto, the dressing being provided in at least one sealed container prior to the removal of the components of the explanted medical device to maintain the dressing a presoaked, sterile condition and to prevent the preservation fluid from evaporating from the dressing, the dressing being wrapped around each individual component of the explanted medical device subsequent to the removal of the explanted medical device to preserve the explanted medical device;

whereby the amount of preservation fluid applied to the dressing is controlled, thereby eliminating the need for a reservoir of fluid to be provided.

10. The kit as recited in claim 9, wherein the sealable containers are bags with a sealing strip provided thereon.

11. The kit as recited in claim 10, wherein at least some of the sealable containers include labeled component containers which identify each component of the explanted medical device.

12. The kit as recited in claim 11, wherein the sealable containers include at least one sealable bag in which the labeled component containers are inserted, thereby providing additional sealing.

13. The kit as recited in claim 10, wherein the preservation fluid is a formalin solution.

14. The kit as recited in claim 13, wherein the preservation fluid is a solution of approximately 10% buffered formalin.

15. The kit as recited in claim 13, wherein the dressing is gauze.

16. A kit for the packaging and shipping of components of an explanted medical device which allows all of the components of the explanted medical device to be properly preserved for later examination, the kit comprising:

an insulated box;

sealable containers to individually package the components of the explanted medical device, at least some of the sealable containers include labeled component containers which identify each component of the explanted medical device;

a sterile dressing presoaked in a formalin solution, the dressing is non-abrasive to the components of the explanted medical device and is inert with respect to the formalin solution applied thereto, the dressing being provided in at least one sealed container prior to the removal of the explanted medical device to maintain the dressing a presoaked, sterile condition and to prevent the formalin solution from evaporating from the dressing, the dressing being wrapped around each individual component of the explanted medical device subsequent to the removal of the explanted medical device to preserve the explanted medical device;

packaging material to protect the components of the explanted medical device from physical damage during shipping;

cooling devices to maintain the components of the explanted medical devices at a temperature to prevent the degradation of the explanted medical device during shipping;

whereby the amount of formalin solution applied to the dressing is controlled, thereby eliminating the need for a reservoir of fluid formalin solution to be provided.

\* \* \* \* \*